United States Patent
Chaplin et al.

(10) Patent No.: US 7,026,144 B2
(45) Date of Patent: Apr. 11, 2006

(54) PROCESS FOR PREPARING (-) MENTHOL AND SIMILAR COMPOUNDS

(75) Inventors: Jennifer Ann Chaplin, San Diego, CA (US); Neil Stockenstrom Gardiner, Pretoria (ZA); Robin Kumar Mitra, Benoni (ZA); Christopher John Parkinson, Modderfontein (ZA); Madrie Portwig, Greenside (ZA); Butana Andrew Mboniswa, Edenvale (ZA); Melanie Daryl Evans-Dickson, Livingstone (ZM); Dean Brady, Midrand (ZA); Stephanus Francois Marais, Garsfontein (ZA); Shavani Reddy, Edenvale (ZA)

(73) Assignee: CSIR, Pretoria (ZA)

( * ) Notice: Subject to any disclaimer, the term of this patent is extended or adjusted under 35 U.S.C. 154(b) by 377 days.

(21) Appl. No.: 10/312,996

(22) PCT Filed: Jun. 11, 2001

(86) PCT No.: PCT/IB01/01008

§ 371 (c)(1),
(2), (4) Date: Mar. 27, 2003

(87) PCT Pub. No.: WO02/04384

PCT Pub. Date: Jan. 17, 2002

(65) Prior Publication Data

US 2003/0153031 A1  Aug. 14, 2003

(30) Foreign Application Priority Data

Jul. 7, 2000 (ZA) ............................ 2000/3417

(51) Int. Cl.
*C12P 7/62* (2006.01)
*C12P 7/22* (2006.01)
*C12P 41/00* (2006.01)

(52) U.S. Cl. ................. 435/135; 435/156; 435/280
(58) Field of Classification Search ............. 435/135, 435/280, 156

See application file for complete search history.

(56) References Cited

U.S. PATENT DOCUMENTS 5,403,739 A * 4/1995 Ikushima et al. .......... 435/280
6,600,060 B1 * 7/2003 Barclay et al. ............ 554/224

FOREIGN PATENT DOCUMENTS

DE   538 376 C   11/1931
DE   568 671 C   1/1933

OTHER PUBLICATIONS

Langrand et al "Lipase-catalyzed ester formation in organic solvents an easy preparative resolution of alpha-substuted cyclohexanols" Tetrahedron Letters vol. 26, No. 15 pp 1857-1860 1985.*

(Continued)

*Primary Examiner*—Herbert J. Lilling
(74) *Attorney, Agent, or Firm*—Sterne, Kessler, Goldstein & Fox P.L.L.C.

(57) ABSTRACT

A process of separating a single desired stereoisomer from a racemic mixture of eight stereoisomers of a compound of formula (III), wherein $R_1$ represents an isopropanol group, an isopropyl group or an isopropylene group, includes the steps of: contacting the racemic mixture in a suitable organic solvent with an esterifying agent and a stereospecific enzyme which stereoselectively esterifies the —OH group of the desired stereoisomer, for a time sufficient to convert a desired percentage of the desired stereoisomer to a compound of formula (IV), wherein $R_1$ is as defined above and $R_4$ is an alkyl or an aryl group, to give a first reaction product including the compound of formula (IV), the organic solvent, the unconverted stereoisomers of the compound of formula (III), excess esterifying agent and by-products of the reaction; and separating the compound of formula (IV) from the first reaction product. The process is of particular application for the production of (−)-menthol

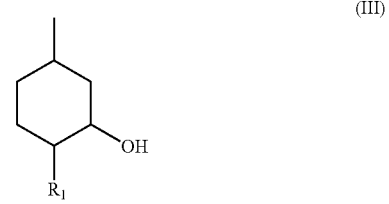

(III)

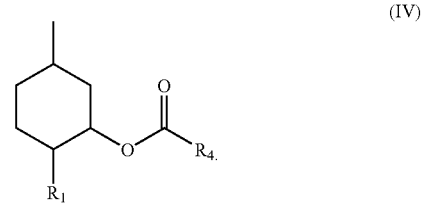

(IV)

18 Claims, No Drawings

OTHER PUBLICATIONS

Shimada et al "Enzymatic Synthesis of L-menthyl esters in organic solvent-free system" JAOCS vol. 76 No. 10 pp 1139-1142 (1999).*

Cambou et al "Preparative Production of Optically Active esters and alcohols using esterase-catalyzed stereospecific transesterification in organic media" Jour American Chem Society vol. 106, No. 9 pp 2687-2692 1984.*

Cernia, E. et al., The Role of the Reaction Medium in Lipase-catalyzed Esterifications and Transesterifications; Chemistry and Physics of Lipids, vol. 93 (1998); p. 157-168.

* cited by examiner

PROCESS FOR PREPARING (-) MENTHOL AND SIMILAR COMPOUNDS

BACKGROUND TO THE INVENTION

THIS invention relates to a process for producing (−)-menthol and similar compounds.

(−)-Menthol is one of the world's largest selling flavour compounds, with a production of about 11800 tons per annum. Its peppermint flavour and cooling sensation are used in many products, primarily in mentholated cigarettes and oral hygiene products, such as toothpaste, mouthwash and chewing gum. Pharmaceutical and healthcare products use menthol in a variety of product types, such as cough lozenges, shaving cream and topical analgesics.

Owing to seasonal variations and poor farming practices, the availability of natural menthol from the largest supplying countries, India and China, is sometimes erratic. In addition to this, only a limited amount of peppermint can be planted, thus limiting the supply of natural menthol. The remainder of the demand for menthol is met by synthetic menthol.

Organoleptically, natural and synthetic menthol are completely interchangeable; any slight differences have been largely eliminated through product development. Moreover, synthetic menthol has a purer and more consistent taste and odour profile since it does not contain the impurities present in natural menthol.

There is always a need for new processes for the production of (−)-menthol and similar compounds.

SUMMARY OF THE INVENTION

According to the invention there is provided a process of separating a single desired stereoisomer from a racemic mixture of eight stereoisomers of a compound of the formula III

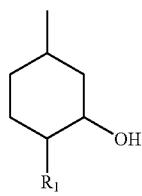

III wherein $R_1$ represents an isopropanol group, an isopropyl group or an isopropylene group, including the steps of:

(1) contacting the racemic mixture in a suitable organic solvent with an esterifying agent and a stereospecific enzyme which stereoselectively esterifies the —OH group of the desired stereoisomer, for a time sufficient to convert a desired percentage of the desired stereoisomer to a compound of the formula IV

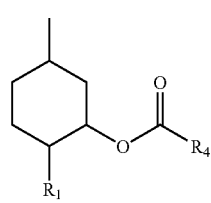

IV wherein $R_1$ is as defined above and $R_4$ is an alkyl or an aryl group, to give a first reaction product including the compound of the formula IV, the organic solvent, the unconverted stereoisomers of the compound of the formula III, excess esterifying agent and by-products of the reaction; and (2) separating the compound of the formula IV from the first reaction product.

Step (2) preferably comprises the sub-steps of:

(2)(a) separating the first reaction product from the enzyme;

(2)(b) removing from the first reaction product the organic solvent, the excess esterifying agent, and the by-products of the reaction to give a second reaction product including the compound of the formula IV and the unconverted stereoisomers of the compound of formula III; and (2)(c) separating the compound of the formula IV from the second reaction product leaving a third reaction product containing the unconverted stereoisomers of the compound of the formula III.

The process of the invention preferably includes a further step, step (3) of:

(3) racemizing the unconverted stereoisomers of the compound of the formula III in the third reaction product to give a fourth reaction product containing a mixture of all eight stereoisomers of the compound of the formula III and recycling the fourth reaction product to step (1).

The process of the invention preferably includes a further step, step (4) of:

(4) hydrolysing the compound of the formula IV to give the desired stereoisomer of the compound of the formula III.

In the process of the invention, when $R_1$ is an isopropanol group or an isopropylene group, before or after step (4), the compound of the formula IV or the desired stereoisomer of the compound of the formula III may be subjected to a reduction step to convert $R_1$ to an isopropyl group.

The process of the invention preferably includes the following steps, prior to step (1) of:

(a) reacting a compound of the formula I

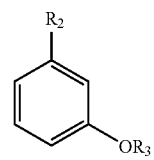

I wherein $R_2$ represents a methyl or a hydroxymethyl group, and $R_3$ represents H, a base metal, a benzyl group or an allyl group, with an alkylating agent in the presence of a catalyst to give a compound of the formula II

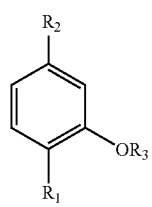

II wherein $R_1$, $R_2$ and $R_3$ are as defined above; and (b) hydrogenating the compound of the formula II in the presence of a catalyst to give a racemic mixture of the eight stereoisomers of the compound of the formula III.

DESCRIPTION OF EMBODIMENTS

The crux of the invention is a process of separating a single desired stereoisomer of a compound of the formula III from a racemic mixture of the eight stereoisomers of the compound of the formula III, by esterification using a stereospecific enzyme.

This process step may form part of a larger process as described below.

The first step, step (a) of the process is to alkylate a compound of the formula I to yield a compound of the formula II, using an alkylating agent such as propylene, isopropanol or acetone, in the presence of a catalyst.

The catalyst may be a Lewis acid catalyst such as $AlCl_3$, $SnCl_4$, $BF_3$, $ZnCl_2$ or $FeCl_3$; or a Brønsted acid such as HCl, HF, $H_2SO_4$ or $H_3PO_4$; or a suitable supported catalyst such as "ENVIROCAT EPIC" which is a polyphosphoric acid on a support, or "ENVIROCAT EPZ 10" which is a ferric chloride on a support; or a solid phosphoric acid; or a suitable zeolite catalyst which is the preferred catalyst.

Step (a) may be carried out in the presence of a solvent such as a chlorinated solvent, e.g dichloromethane, chloroform or dichloroethane, but the presence of a solvent is not essential.

Step (a) may be carried out as a batch reaction or as a continuous gas or liquid phase reaction.

In step (a), the reaction temperature during and after the reaction may be any temperature below 450° C.

Step (a) may be carried out in air or under an inert atmosphere such as argon or nitrogen.

The compound of the formula I is preferably m-cresol, and thus the compound of the formula II is preferably thymol.

At the end of step (a), the catalyst is removed or deactivated, and any solvent present is removed. The required compound of the formula II is isolated from the reaction mixture, for example by distillation. The unreacted alkylating agent and reaction by-products may be recycled to step (a).

The second step, step (b) of the process is to reduce the compound of the formula II to a racemic mixture of the eight stereoisomers of the compound of the formula III, by hydrogenation using hydrogen gas over a suitable catalyst.

The catalyst may be any catalyst typically used in homogeneous catalytic hydrogenations such as $Pd(OAc)_2$ or in heterogenous catalytic hydrogenations such as supported palladium, platinum, rhodium, ruthenium, nickel, sponge nickel and $2CuO.Cr_2O_3$.

The preferred catalyst is a nickel catalyst.

The catalyst loading may be from 0.01 to 20%, preferably from 0.5 to 5%.

Step (b) may be carried out with or without a solvent. If a solvent is used, it may be any solvent typically used for catalytic hydrogenation, for example a hydrocarbon or aqueous caustic.

Step (b) is preferably carried out at an elevated temperature of from 80° C. to 300° C. inclusive, preferably from 160° C. to 200° C. inclusive.

Step (b) is carried out using a hydrogen pressure which is below 50 bar, preferably between 5 and 35 bar inclusive.

When the compound of the formula II is thymol, there is formed a racemic mixture of the four pairs of diastereomeric isomers of menthol, viz (±)-menthol, (±)-isomenthol, (±)-neomenthol and (±)-neoisomenthol, as well as two intermediates (±)-menthone and (±)-isomenthone.

At the end of step (b), the catalyst is removed, e.g by filtration, or is deactivated, and any solvent present is removed.

The next step of the process of the invention, step (1), is the key step of the process.

The racemic mixture of the eight stereoisomers of the compound of the formula III from the hydrogenation step (step (b)) is contacted in a suitable organic solvent with an esterifying agent and with a stereospecific enzyme which stereoselectively esterifies the —OH group of the desired stereoisomer of the compound of the formula III, for a time sufficient to convert a desired percentage of the desired stereoisomer to a compound of the formula IV, to give a first reaction product including the compound of the formula IV, the organic solvent, the unconverted stereoisomers of the compound of the formula III, excess esterifying agent, and by-products of the reaction.

The reaction is a stereoselective esterification of a desired stereoisomer of the compound of the formula III, with the other stereoisomers of the compound of the formula III remaining substantially unchanged, although small amounts of the other stereoisomers may also be esterified by the enzyme.

When $R_1$ of the compound of the formula III is an isopropyl group, the compound corresponds to menthol which consists of eight stereoisomers. The desired stereoisomer of menthol is the (–)-isomer, which can be selectively esterified using a suitable enzyme to the (–)-menthyl ester.

The suitable organic solvent may be any solvent typically used for enzyme catalysed esterification reactions, including isooctane; n-heptane; decane; methyl cyclohexane; t-butyl methyl ether; xylene; kerosene (C5–C6 paraffins, kerasol 60/115), (C7–C8 paraffins, kerasol 94/125); pentane; cyclohexane; hexane; benzene; butanol; toluene; isopropanol; ethyl lactate; and acetone.

The preferred organic solvent is n-heptane.

The amount of the organic solvent used relative to the racemic mixture of the compound of the formula III is preferably in the range of from 5% to 80% racemic mixture to 95% to 20% organic solvent on a volume basis.

When the organic solvent is n-heptane, the racemic mixture is preferably used in an amount of 20% v/v in the n-heptane.

The esterifying agent may be any suitable esterifying agent such as for example vinyl acetate, butyl acetate, octanoic acid, isopropenyl acetate, vinyl butyrate, ethyl lactate and ethyl acetate.

The preferred esterifying agent is vinyl acetate.

The esterifying agent may be used in an molar ratio to the desired stereoisomer of the compound of the formula III of 0.5:1 up to 30:1. The preferred molar ratio of the esterifying agent to the desired stereoisomer of the compound of the formula III is about 2:1 when vinyl acetate is used as the esterifying agent.

The enzyme is a stereospecific enzyme which stereoselectively esterifies the —OH group of the compound of the formula III.

The enzyme may be contained within a microorganism, or secreted into a medium required for microorganism growth, or may be available commercially in semi-purified or purified form. Microorganisms can also be provided with the ability to produce a suitable enzyme through the process of genetic engineering of the microorganism.

Examples of enzymes and microorganisms that are capable of performing this esterifying process include those exhibiting lipase, esterase or protease-like activity.

Suitable enzymes include, but are not limited to:

Enzymes supplied by Fluka: Candida cylindracea lipase, lipase Hog pancreas, lipase *Pseudomonas fluorescens*, lipase *Aspergillus oryzae*, lipase *Rhizopus niveus*, lipase *Rhizomucor miehei*, lipase *Candida antarctica*, lipase *Mucor javanicus*, lipase *Rhizopus arrhizus*, lipase *Penicillium roqueforti*, lipase *Candida lipolytica*, lipoprotein lipase *Pseudomonas* sp., type B, lipoprotein lipase *Pseudomonas cepacia*, lipoprotein lipase *Chromobacterium viscosum*, esterase *Bacillus thermoglucosidasius*, esterase *Bacillus stearothermophilus*, esterase *Mucor miehei*, esterase hog liver;

Enzymes supplied by Altus: *Candida rugosa* lipase, lipase *Mucor miehei*, *Candida antarcitica* B lipase, *Candida antarctica* A lipase, "CHIRO-CLEC-CR," "CHIRO-CLEC-CR" (slurry), porcine liver esterase, Penicillin acylase, Subtilisin Carlsberg, "CHIRO-CLEC-BL" (slurry), "CHIRO-CLEC-PC" (slurry), "CHIRO-CLEC-EC" (slurry), *Aspergillus oryzae* protease, "PEPTICLEC-TR" (slurry);

Enzymes supplied by Recombinant Biocatalysis: "ESL-001-01," "ESL-001-01," with stabiliser "ESL-001-02," "ESL-001-03," "ESL-001-05;"

Enzymes supplied by Boebringer-Mannheim: "CHIRAZYME L4" (*Pseudomonas* sp.), "CHIRAZYME L5" (*Candida antarctica* fraction A), "CHIRAZYME L1" (Burkholderia), "CHIRAZYME L6" (Porcine pancreas), "CHIRAZYME L7," "CHIRAZYME L8;"

Enzymes supplied by Gist-Brocades: Naproxen esterase, "LIPOMAX," "GENZYME," Lipoprotein lipase;

Enzymes supplied by Novo: "NOVOZYME 868," "NOVOZYME 435," immobilised *Candida antarctica* lipase, Nagase enzyme, "LIPASE A-10FG" (*Rhizopus javanicus*);

Enzymes supplied by Amano: "AMANO AYS," "AMANO PS," "AMANO PSD," "AMANO AKD11," "AMANO AKD111."

The preferred enzyme is "AMANO AK" lipase enzyme supplied by Amano of Japan.

The enzyme may be used either in the free form or immobilized on a suitable support which may be diatomaceous earth.

The enzyme is preferably used in an amount of from 1 g/l to 60 g/l of the reaction mixture, i.e the racemic mixture of the eight stereoisomers of the compound of the formula III, the suitable organic solvent and the esterifying agent.

The resolution step is preferably carried out at a temperature of from 20° C. to 100° C. inclusive and at atmospheric or higher pressure. When the enzyme is "AMANO AK," the preferred reaction temperature is about 50° C.

The resolution reaction is continued for a time sufficient to convert a desired percentage of the desired stereoisomer of the compound of the formula III to the compound of the formula IV. Generally, it is desirable that as much as possible of the desired stereoisomer is converted to the compound of the formula IV without the reaction proceeding to the esterification of the other stereoisomers present in the racemic mixture.

The reaction time is preferably about 24 hours or less when the reaction is performed in batch mode.

The next step, step (2)(a) of the process of the invention is to separate the first reaction product from the enzyme so that the enzyme can be recycled. This may be achieved for example by centrifugation or by filtration.

A major advantage of the process of the invention is that it is possible to recycle the enzyme a number of times to the resolution step, so as to improve the economics of the process.

The necessity for enzyme recycle may be eliminated by use of the enzyme in a continuous system wherein the enzyme is retained within a reactor. The racemic mixture of the compound of the formula III, the organic solvent and the esterifying agent as described above, are fed into the reactor, wherein the desired stereoisomer of the compound of the formula III is esterified to the compound of the formula IV to form the first reaction product The first reaction product typically exits the reactor at a similar rate to the inlet feed, for further processing. The enzyme may typically be retained within the reactor through the use of membranes, or by immobilisation onto a support material, or through stabilisation by cross-linking.

The next step, step (2)(b) of the process of the invention is to remove the organic solvent, the excess esterifying agent and any by-products, to give a second reaction product including the compound of the formula IV and the unconverted stereoisomers of the compound of the formula III. This may be carried out by distillation in which the organic solvent, e.g the n-heptane and the excess esterifying agent, e.g the vinyl acetate, are taken off at the top of the column as a single stream and recycled back to suitable storage tanks for later re-use.

The next step, step (2)(c) of the process of the invention is to separate the compound of formula IV from the second reaction product leaving a third reaction product containing the unconverted stereoisomers of the compound of the formula III. This separation may be achieved by distillation.

In the compound of the formula IV, when $R_1$ is not an isopropyl group, the $R_1$ group can, through a reduction process, be converted to an isopropyl group, either at this stage, or subsequent to hydrolysis of the ester group as described below. This results in the production of the desired stereoisomer of menthyl ester, or subsequent to hydrolysis, in the production of the desired stereoisomer of menthol.

The next step, step (3) of the process of the invention is to racemise the unconverted stereoisomers in the third reaction product to give a fourth reaction product containing a mixture of all eight stereoisomers of the compound of the formula III and recycling this to the resolution step of the process.

The racemisation may be achieved over a suitable catalyst with or without hydrogen gas, with or without a solvent, and at atmospheric or greater pressure.

The step may be carried out with or without a solvent. If a solvent is used, the solvent may be any solvent typically used for catalytic hydrogenation, most typically a hydrocarbon or aqueous caustic.

The catalyst used may be any catalyst typically used in homogeneous catalytic hydrogenations such as $Pd(OAc)_2$ and $Ru(PPh_3)_3Cl_2$, or in heterogeneous catalytic hydrogenations such as supported palladium, platinum, rhodium, ruthenium, nickel, sponge nickel and $2CuO.Cr_2O_3$, or a solid oxide such as celite, CuO, $CrO_3$, CoO, $SiO_2$, $Al_2O_3$, $Ba(OH)_2$, MnO, $Al(iOPr)_3$, $LnO_2$, ZrO and the zeolites.

The reaction may be carried out at any temperature between 80° C. and 300° C. inclusive, preferably at a temperature between 180° C. and 220° C. inclusive.

The hydrogen pressure may be any pressure below 50 bar, preferably between 5 and 35 bar inclusive.

The catalyst loading may be between 0.01 and 20%, preferably between 0.05 and 5%.

At the end of the step, the catalyst is removed or deactivated, and any solvent present is removed.

This racemisation step may be carried out in conjunction with step (b), i.e the hydrogenation step, where appropriate.

The next step, step (4) of the process of the invention is to hydrolyse the compound of the formula IV to the desired stereoisomer of the compound of the formula III. The reaction may be carried out in the presence of a base which may be a salt of a lower aliphatic alcohol such as sodium methoxide or sodium ethoxide, a metal hydroxide such as KOH, NaOH, or $Mg(OH)_2$, or amine bases such as $NH_4OH$.

The reaction may be carried out in any solvent typically used in hydrolysis reactions, such as for example a lower aliphatic alcohol or water. Combinations of the solvents may also be used.

The reaction temperature may be any temperature below the boiling point of the chosen solvent or the reflux temperature of the mixture at the pressure at which the reaction is carried out.

In the compound of the formula IV, where $R_1$ is an isopropyl group, hydrolysis of this compound ((−)-menthyl ester) results in the production of (−)-menthol.

As a final step, the desired isomer of the compound of the formula III may be purified to the desired purity by, for example, distillation or crystallisation.

EXPERIMENTAL WORK

The results of various experiments carried out in relation to the process of the invention are set out below.

EXAMPLE 1 m-Cresol (2.0 g) and o-phosphoric acid (4 mol e.g 8.5 g) were placed in a round bottom flask and heated to 85° C. Isopropanol (1.11 g) was added dropwise over 30 minutes. The reaction was then cooled to 25° C., and the organic phase extracted into toluene (20 ml). NMR analysis of the concentrated organic fraction indicated a 10% conversion of m-cresol to thymol.

EXAMPLE 2

Thymol (4.20 g), cyclohexane (50 ml) and 5% Pt/C (0.40 g) were placed in a 300 ml Parr autoclave reaction chamber. Once sealed, the chamber was flushed with $N_2$ (g) before charging with $H_2$ (g) (20 bar). The reaction was heated to 180° C. and the reaction was allowed to proceed for 2 hours. The reaction was then allowed to cool to room temperature, the pressure inside the reactor was released and the reaction mixture filtered to give a mixture of menthol stereoisomers (100% conversion thymol, 80% selectivity to menthols).

EXAMPLE 3

In 2 ml vials, 10 or 100 mg of *Pseudomonas cepacia* lipase (Fluka), *Pseudomonas fluorescens* lipase (Fluka), penicillin acylase (Altus), subtilisin Carlsberg (Altus), *Aspergillus oryzae* protease and "PEPTICLEC-TR" slurry (Altus) were weighed. To this cyclohexane, hexane, pentane or heptane (962.72 µl) were added. Isomeric menthol (23 µl) and vinyl acetate (14.28 µl) were also added. These vials were incubated at 30° C. or 37° C. for 2 or 48 hours. Enzyme was then removed from the mixture by centrifugation. Samples were analysed by gas chromatography (GC). An individual peak found on each of the chromatograms was identified as that of (−)-menthyl acetate by comparison with the corresponding retention time of a standard sample of (−)-menthyl acetate.

EXAMPLE 4

Lyophilised "AMANO AK" (a *Pseudomonas fluorescens* lipase enzyme) was obtained from Amano Pharmaceutical Co. (Japan). Concentrated liquid menthol was produced by the hydrogenation of thymol. The menthol contained four diastereomeric pairs of menthols, namely (+)-menthol (51%), (±)-isomenthol (14%), (±)-neomenthol (29%) and (±)-neoisomenthol (2%). A volume of 1 ml was added to sealed batch reactors. Vinyl acetate (54 µl) was added at a 2:1 molar ratio to (−)-menthol. Heptane was added as solvent to a final reaction volume of 5 ml. These reactors were incubated in silicon oil baths at 50° C. and stirred on a stirring hot plate. Batch times, unless otherwise stated were 24 hours. The reaction mixture was then centrifuged to separate the products from the enzyme. The supernatant was analysed by GC (% m/m analysis). Of the available (−)-menthol, 100% was converted to (−)-menthyl acetate, at an ee of 98%. The enzyme was recycled a total of 150 times by washing with heptane and adding fresh substrate (liquid menthol, vinyl acetate and heptane) after every recycle. An amount of menthyl acetate equivalent to 185 g of (−)-menthol was produced by this process.

EXAMPLE 5

"AMANO AK" lipase enzyme was dissolved in phosphate buffer (5 mM, pH 7) before adding Celite 535 (in a ratio of 1:2). The mixture was frozen at −80° C. for 5 minutes and then freeze-dried for 24 hours to produce immobilized enzyme. A substrate mixture containing 15.5% (v/v) of liquid menthol and 5.5% (v/v) vinyl acetate and 79% (v/v) of n-heptane was prepared. The mixture was pumped through 5 columns arranged in series packed with immobilised enzyme. The temperature of the reaction was maintained at 50° C. The end product was analysed for the formation of (−)-menthyl acetate by GC analysis. Of the available (−)-menthol, 100% was converted to (−)-menthyl acetate at an ee of 98%. In a 206 day period an amount of (−)-menthyl acetate equivalent to 101 g of menthol per gram of immobilized enzyme was produced by this immobilized enzyme system.

EXAMPLE 6

A solution of methanol (50.1 g), water (50.21 g) and NaOH (6.03 g, 0.15 mol) was placed in a reactor and heated to 60° C. (−)-Menthyl acetate (30.53 g, 15 mol) was then added to the reactor and the reaction was vigorously stirred for 30 minutes. Qualitative GC analysis indicated a 53 area % menthyl acetate and a 47 area % menthol.

EXAMPLE 7

(−)-Menthol (100 g) and Ni (1%) were placed in round bottom flask and heated at reflux for 2 hours. Once cooled to 25° C., the reaction mixture was sampled. Quantitative m/m analysis 17% thymol, 23% menthols and 54% menthones with a % (+)-menthol/(±)-menthol of 22%.

The invention claimed is:

1. A process of separating a single stereoisomer from a racemic mixture of eight stereoisomers of a compound of the formula III:

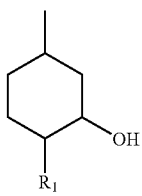

wherein $R_1$ represents an isopropanol group, an isopropyl group or an isopropylene group, including the steps of:
(1) contact the racemic mixture in a suitable organic solvent with an esterifying agent and a stereospecific enzyme which stereoselectively esterfies the —OH group of the single stereoisomer, for a time sufficient to convert the single stereoisomer to a compound of the formula IV without the reaction proceeding to the esterification of any of the other of the eight stereoisomers of the racemic mixture:

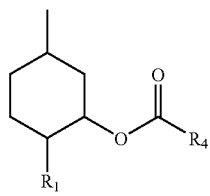

wherein $R_1$ is as defined above and $R_4$ is an alkyl or an aryl group, to give a first reaction product including the compound of the formula IV, the organic solvent, the unconverted stereoisomers of the compound of the formula III, excess esterfying agent and by-products of the reaction; and
(2) separating the compound of the formula IV from the first reaction product.

2. A process according to claim 1 wherein step (2) comprises the sub-steps of:
(2)(a) separating the first reaction product form the enzyme;
(2)(b) removing from the first reaction product the organic solvent, the excess esterifying agent, and the by-products of the reaction to give a second reaction product including the compound of the formula IV and the unconverted stereoisomers of the compound of formula III; and
(2)(c) separating the compound of the formula IV from the second reaction product leaving a third reaction product containing the unconverted stereoisomers of the compound of the formula III.

3. A process according to claim 1 including the step, after step (2) of:
(3) racemizing the unconverted stereoisomers of the compound of the formula III in the third reaction product to give a fourth reaction product containing a mixture of all eight stereoisomers of the compound of the formula III and recycling the fourth reaction product to step (1).

4. A process according to claim 3 including the step, after step (3) of:
(4) hydrolysing the compound of the formula IV to give the single stereoisomer of the compound of the formula III.

5. A process according to claim 4 wherein when $R_1$ is an isopropanol group or an isopropylene group, before or after step (4), the compound of the formula IV or the single stereoisomer of the compound of the formula III is subjected to a reduction step to convert $R_1$ to an isopropyl group.

6. A process according to claim 1 including the following steps, prior to step (1) of:
(a) reacting a compound of the formula I

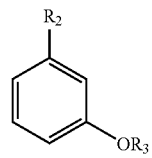

wherein $R_2$ represents a methyl or a hydroxymethyl group, and $R_3$ represents H, a base metal, a benzyl group or an allyl group,
with an alkylating agent in the presence of a catalyst to give a compound of the formula II

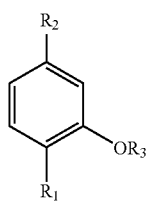

wherein $R_1$ is as defined in claim 1 and $R_2$ and $R_3$ are as defined above; and
(b) hydrogenating the compound of the formula II in the presence of a catalyst to give a racemic mixture of the eight stereoisomers of the compound of the formula III.

7. A process according to claim 1 wherein in step (1) the solvent is selected from the group consisting of isooctane; n-heptane; decane; methyl cyclohexane; t-butyl methyl ether; xylene; kerosene; pentane; cyclohexane; hexane; benzene; butanol; toluene; isopropanol; ethyl lactate; and acetone.

8. A process according to claim 7 wherein in step (1) the solvent is n-heptane.

9. A process according to claim 1 wherein in step (1) the esterifying agent is selected from the group consisting of vinyl acetate, butyl acetate, octanoic acid, isopropenyl acetate, vinyl butyrate, ethyl lactate and ethyl acetate.

10. A process according to claim 9 wherein in step (1) the esterifying agent is vinyl acetate.

11. A process according to claim 1 wherein in step (1) the esterifying agent is used in a molar ratio to the single stereoisomer of the compound of the formula III of 0, 5:1 to 30:1 inclusive.

12. A process according to claim 1 wherein in step (1) the stereospecific enzyme is used in an amount of from 1 g/l to 60 g/l inclusive of the mixture of the racemic mixture of the eight stereoisomers of the compound of the formula III, the suitable organic solvent and the esterifying agent.

13. A process according to claim 1 wherein step (1) is carried out at a temperature of from 20° C. to 100° C. inclusive and at atmospheric or higher pressure.

14. A process according to claim 2 wherein after step (2)(a) the stereospecific enzyme is recycled to step (1).

15. A process according to claim 2 wherein in step (1) the stereospecific enzyme is used in a continuous system wherein the stereo specific enzyme is retained within a reactor and wherein in step (2)(a) the first reaction production exits the reactor leaving behind the enzyme.

16. A process according to claim 4 wherein in step (4) the hydrolysis is carried out in the presence of a base, in a suitable solvent, and at a temperature below the boiling point of the solvent or the reflux temperature of the mixture of reactants at the pressure at which the reaction is carried out.

17. A process to claim 1 wherein in the compound the formula III, $R_1$ represents an isopropyl group.

18. A process according to claim 2 including the step, after step (2) of:
  (3) racemizing the unconverted stereoisomers of the compound of the formula III in the third reaction product to give a fourth reaction product containing a mixture of all eight stereoisomers of the compound of the formula III and recycling the fourth reaction product to step (1).

* * * * *